United States Patent [19]
Pinchuk et al.

[11] Patent Number: 4,905,367
[45] Date of Patent: Mar. 6, 1990

[54] MANUFACTURE OF STRETCHABLE POROUS SUTURES

[75] Inventors: Leonard Pinchuk; John B. Martin, both of Miami, Fla.

[73] Assignee: Corvita Corporation, Miami, Fla.

[21] Appl. No.: 268,745

[22] Filed: Nov. 8, 1988

[51] Int. Cl.$^4$ .............................................. B23P 25/00
[52] U.S. Cl. ....................................... 29/458; 29/459; 606/231
[58] Field of Search .......................... 128/335.5, 334 R; 29/458, 459

[56] References Cited

U.S. PATENT DOCUMENTS 4,355,426 10/1982 MacGregor .
4,470,941 9/1984 Kurtz ................................ 128/335.5
4,475,972 10/1984 Wong .
4,712,553 12/1987 MacGregor .

*Primary Examiner*—P. W. Echols
*Assistant Examiner*—Irene Cuda
*Attorney, Agent, or Firm*—Lockwood, Alex, Fitzgibbon & Cummings

[57] ABSTRACT

A method is provided for manufacturing surgical sutures that have an elastomeric and porous structure. The elastomeric and porous structure is formed from a mixture including a polymer material and an elutable solvent therefor, which mixture is extruded into an aqueous liquid and pulled therethrough.

14 Claims, 1 Drawing Sheet

MANUFACTURE OF STRETCHABLE POROUS SUTURES

BACKGROUND AND DESCRIPTION OF THE INVENTION

The present invention generally relates to the manufacturing of surgical sutures that are stretchable and that have a porous structure, the suture being of the non-braided and non-woven type and having a surface porosity that provides an environment that is conducive to tissue ingrowth into the pores of the porous surface. The method includes forming the porous suture from a mixture of elastomeric polymer and elutable organic solvent materials, which mixture is extruded into the configuration of a strand or a suture, after which the extruded strand is passed through a trough or the like containing a liquid which elutes the organic solvent from the strand in order to form the porous surface of the stretchable suture.

Most sutures which are available today for the repair, fixation and/or approximation of body tissues during surgical procedures are composed of single strands or multiply braided strands of flexible material, with or without a needle attached to one or both ends of the flexible material. Sutures which are used for the attachment of prosthetic devices or implants to body tissues have especially stringent requirements regarding strength, biocompatibility, flexibility, sterilizability and, in some cases, biodegradability. An especially desirable property for sutures that are intended for specialized uses such as those involving biologic, synthetic or biosynthetic vascular grafts is to provide the suture with porosity that extends to the external surface of the suture and that provides for rapid tissue ingrowth and endothelialization, as well as other important properties. An example of a porous suture is found in MacGregor U.S. Pat. No. 4,712,553.

Providing prosthetic devices and implants with porous surfaces has been developed in order to promote the implantation of such devices. Porous coatings or surfaces have been implemented on or proposed in connection with devices such as heart valves, cardiac pacers and electrodes thereof, vascular grafts, blood pumps, ventricular assist devices, artificial hearts, flexible heart valve members, bloodstream filters, intracardiac patches, diaphragms or baffles, vascular access tubes, and the like. One of the objectives of providing porous surfaces on these types of devices and implants is to promote colonization and tissue ingrowth into the depth of the porous surface from adjacent body tissue in order to provide bonding between the body tissue host and the porous member. Typically, the body tissue ingrowth is combined with the promotion of tissue growth into the porous surface from the nucleated bloodstream cells. Such porous surfaces provide a porous depth that affords a means of fixation to host tissues by soft tissue growth into the porous depth of the surface, and they provide tissue-implant interfaces which are blood compatible arising from colonization and tissue formation on the blood-contacting surfaces.

Imparting stretching and porosity to sutures according to the present invention has been found to provide advantageous properties including exceptional compliance between the host tissue and the implant device or the like while simultaneously permitting body tissue ingrowth into the pores of the suture in order to accelerate the healing process. The property of exceptional compliance of the stretchable suture assists the suture in being able to yield to bending under stress conditions imparted by sewn and/or knotted suture assemblies. By allowing tissue ingrowth into the interstices of the porous suture, potential dead spaces are reduced or eliminated thus making the suture less prone to primary or secondary infection. The stretchable porous suture also provides the possibility for reduced intimal hyperplasia and stenotic narrowing at the anastomotic site. The generally compressible nature of the stretchable porous suture made according to the invention permits the use of a needle whose diameter is less than that of the suture itself in order to thereby reduce blood leakage at suture sites in vascular anastomoses.

Additionally, the elastomeric properties and surface irregularities that are associated with the stretchable porous suture structure according to this invention result in less slippage when the suture is tied in order to provide a more secure knot than that achieved by using smooth or monofilament sutures that are not elastomeric. The porous suture structure also provides a favored environment for the controlled release of drugs to promote healing and/or to resist infection. Porous stretchable sutures according to this invention can be made of the same material as, and be provided with a surface structure that is similar to, the device being implanted with the aid of the suture, such as a synthetic graft, with the result that the suture material will demonstrate substantially the same physical and chemical properties as the device being sutured. This can be of assistance in promoting more uniform healing because the surface free energy of the porous suture will be similar to that of the graft being secured thereby. If desirable, the porous suture can be bonded to the vascular graft or the like, which is facilitated when the suture and the graft are made of substantially the same material.

These various properties and advantages have been attained by the present invention, by which a non-braided stretchable surgical suture is provided which includes an exterior portion having a porous structure, such exterior portion being between the outer surface of the suture and a location internal thereof to provide a porous surface or layer. Manufacturing the porous stretchable suture includes elution from a continuous elongated polymeric member which exhibits substantial elastomeric properties when extruded into a strand from a combination of the polymer and an organic solvent for the polymer. The method includes eluting the organic solvent from the extruded strand by passing same through a liquid which leaches or elutes the organic solvent from the strand.

It is accordingly a general object of the present invention to provide a method for producing an improved surgical suture.

Another object of this invention is to provide a method for forming an improved surgical suture that has pores generally external thereof.

Another object of the present invention is to provide an improved method for forming a surgical suture that is of the non-braided, non-woven type, while still having compressible qualities for reducing blood leakage at suture sites in vascular anastomoses.

Another object of the present invention is to provide an improved method for extruding a surgical suture that permits body tissue ingrowth into an external portion thereof that provides a porous surface.

Another object of this invention is to provide an improved method for manufacturing a porous surgical suture for accelerating the healing process and for reducing the likelihood of primary or secondary infection.

Another object of the present invention is to provide an improved method for forming a surgical suture that can be made from the same material and can be provided with the same surface structure as a synthetic graft or the like that is being fixed in place by the suture.

Another object of this invention is to provide an improved method for forming a surgical suture provided with surface irregularities which lessen the likelihood of slippage when the suture is tied and which provide a favored environment for the controlled release of drugs to promote healing and/or to resist infection.

Another object of the present invention is to provide an improved method for providing a surgical suture that is stretchable, particularly in the axial direction.

Another object of this invention is to provide an improved manufacturing method for a surgical suture that exhibits improved matching or compliance between host tissue and a graft or the like.

These and other objects, features and advantages of this invention will be clearly understood through a consideration of the following detailed description.

BRIEF DESCRIPTION OF THE DRAWINGS

In the course of this description, reference will be made to the attached drawings, wherein.

DESCRIPTION OF THE PARTICULAR EMBODIMENTS

Figure 2:
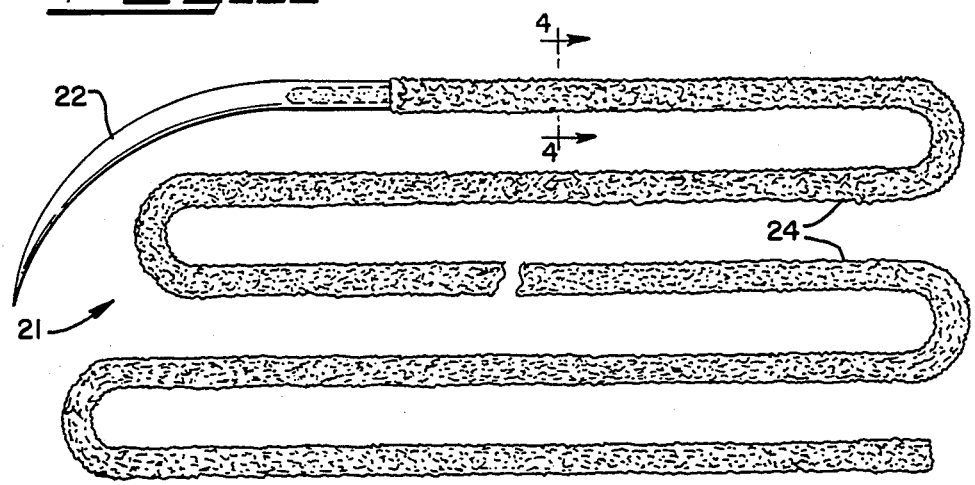
FIG. 2 is an elevational view of a typical suture made in accordance with the method of this invention.
Figure 3:
FIG. 3 is an enlarged perspective view of a portion of the suture shown in FIG. 2.
Figure 4:
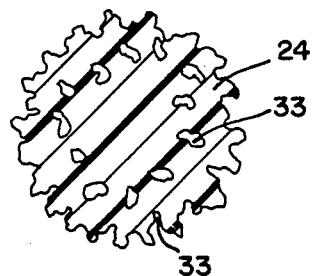
FIG. 4 is a cross-section along the line 4—4 of FIG. 2.
Figure 5:
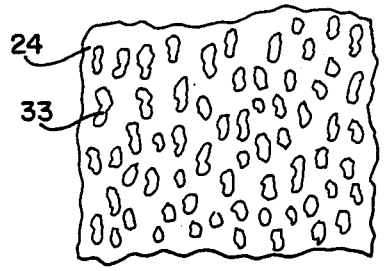
FIG. 5 is a sketch of a portion of a stretchable suture made according to the invention which has been further enlarged.

An assembly including a length of suture material generally designated as 21 together with a suture needle 22 is illustrated in FIG. 2. Needle 22 is attached to the suture material 21 by crimping, swaging or the like. Preferably, the suture needle 22 has an outside diameter that is smaller than the uncompressed outside diameter of the suture material 21 in order to assist in reducing or preventing leakage along the suture line during and after surgery, this feature being possible in large measure due to the radial compressibility of the elastomeric suture material 21. The illustrated suture material includes a porous elongated portion 24 which is in the form of an elastomeric generally cylindrical elongated porous polymeric strand or monofilament.

Figure 1:
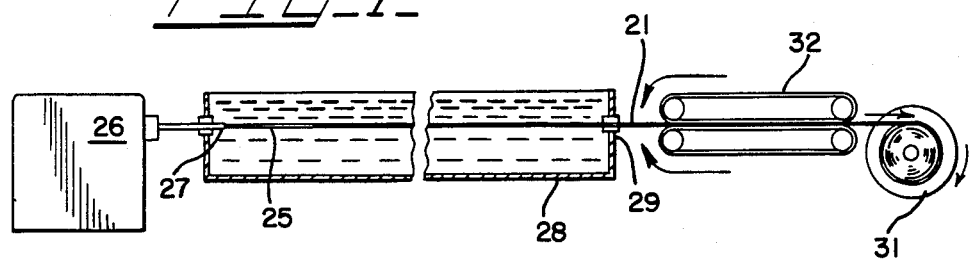
FIG. 1 is an elevational view, partially in cross-section, of a typical apparatus suitable for use in manufacturing a stretchable porous suture in accordance with this invention.

Regarding the apparatus illustrated in FIG. 1, such includes an extruder or distributor 26 for directing a filament or strand 25, typically in conjunction with formation of same by extrusion techniques, toward an elongated body of liquid. The relationship between outlet nozzle 27 of the distributor 26 and the body of liquid ensures that the strand 25 enters the body of liquid promptly after it leaves the nozzle 27. Generally speaking, the body of liquid will be contained within an elongated enclosure 28. In this regard, the strand 25 may exit the outlet nozzle 27 at a location generally above one end of the elongated enclosure 28 and then drop into the liquid therewithin. Alternatively, as illustrated in FIG. 1, the outlet nozzle 27 can be positioned below the surface of the liquid within the elongated enclosure 28 whereby the strand 25 engages the liquid immediately upon its exit from the outlet nozzle 27.

Strand 25 is pulled through the liquid within the elongated enclosure 28. Strand 25 can exit at a location above the elongated enclosure 28, or it can exit through an orifice 29 within a wall, such as a vertical wall, of the elongated enclosure 28. In this manner, all surfaces of the strand 25 can remain in contact with the liquid for a relatively lengthy time period in order to complete the desired leaching or elution so as to form the elastomeric suture material 21. Pulling of the strand 25 through the elongated enclosure 28 can be accomplished by any suitable means, such as the illustrated take-up roll 31.

Because of the elastomeric nature of the suture material 21, it is generally preferred to spread out axially directed forces which are applied to the suture material 21 so that it can be collected on the take-up roll 31 or the like. A suitable approach in this regard is to position a longitudinal gripper assembly 32 closely downstream of the elongated enclosure 28. Gripper assembly 32 includes generally opposing conveyor members which longitudinally engage the suture material 21 and convey same toward the take-up roll 31 or the like. It is generally desirable that take-up roll 31, gripper assembly 32 and the like convey the suture material 21 at a rate slightly faster than the rate the strand 25 leaves the distributor 26 through outlet nozzle 27. This will maintain tension on the strand 25 as it passes through the elongated enclosure 28.

Sizes of suture material 21 can range between that of a 12-0 U.S.P. size suture having an outer diameter as small as 0.001 mm and a U.S.P. size 2 suture having an outer diameter as large as about 0.599 mm. Thus, suture material 21 may have an outside diameter between about 0.001 mm and about 0.6 mm and above, depending upon the desired suture use. Typical sizes of suture material 21 according to this invention include a 7-0 suture material having a diameter of between about 0.050 and 0.069 mm, while the diameter of a 6-0 suture material is on the order of between about 0.070 and 0.099 mm. The average size of each pore 33 of the porous elongated portion 24 is on the order of about 0.005 and about 0.060 mm.

The size, shape and density of the pores 33 of the suture material 24 illustrated in FIGS. 2, 3, 4 and 5 are determined to a substantial degree by the elutable materials included in the polymer material when it leaves the nozzle 27. Strand 25 is composed of a mixture of an elastomeric polymeric material and elutable solvent material which is dissolved out within the elongated enclosure 28 to form a plurality of pores 33. This mixture of polymeric material and elutable material may be extruded as a solid cylinder. Subsequent elution of this solid cylinder forms the stretchable, porous suture material 21 that includes the eluted pores 33.

Porous suture material 21 is a stretchable and flexible non-metallic elastomeric material that is either inert or biodegradable. A suitable polymeric strand 25 is axially stretchable to a substantial extent, typically up to about twice its initially extruded length, or more. Stretchability can be greater than 300 percent, even up to about 600 percent axial stretch. The polymerized materials include polyurethanes which are biocompatible and exhibit superior elastomeric properties and flexibility. The elutable materials are solvents for the particular polymer material that is used. Elutable materials are generally water-soluble materials that are readily leached by the utilization of water or water blends as the elution medium. Organic solvents are preferred. In a general sense, a solvent exchange takes place within the elongated enclosure 28, which contains an aqueous liquid. The aqueous liquid coagulates the organic solvent present in the polyurethane, and the organic solvent is replaced by the aqueous liquid or water, which runs out of or evaporates from the pores 33 thus formed.

Pores 33 are formed by what may be called a phase inversion technique. The aqueous liquid is a non-solvent of the polyurethane, while the organic solvent which is mixed with the extruded strand 25 is a solvent for polyurethane. Such solvent is miscible with water, or it is at least reasonably soluble therein or within an aqueous blend such as an alcohol-water mixture. Accordingly, the organic solvent leaves the polyurethane after it is in extended contact with the aqueous liquid. When the polyurethane initially engages the aqueous liquid, it gives a general appearance of polymer beads that have precipitated within a non-solvent therefor.

This solvent exchange approach can be enhanced by extending the length of time that the extruded strand 25 is in contact with the aqueous liquid. Also advantageous is the use of an aqueous liquid which is a blend of water with a low molecular weight or short carbon chain alcohol such as ethanol. Applying a negative pressure within the elongated enclosure 28 or heating the aqueous liquid to above room temperature can also enhance the needed exchange of the organic solvent with the aqueous liquid.

The organic solvents to be used include those which mix with or can be extruded with a urethane while being also water-soluble or soluble in a water-alcohol blend. Included are dimethylacetamide, dimethylformamide, dimethyl sulfoxide, tetrahydrofuran, pyrrole, and the like.

It will be understood that the embodiments of the present invention which have been described are illustrative of some of the applications of the principles of the present invention. Numerous modifications may be made by those skilled in the art without departing from the true spirit and scope of the invention.

We claim:

1. A method for manufacturing a non-braided porous and elastomeric surgical suture, comprising:
    combining an elastomeric polymer material with an organic solvent for the polymer material in order to form an extrudable mixture;
    extruding said extrudable material into an elongated strand including an extrusion of said polymer material having said organic solvent interspersed with the polymer material;
    passing said extruded elongated strand of polymer material interspersed with said organic solvent into and through a supply of liquid within which said organic solvent is soluble and within which said polymer material is substantially insoluble, said passing step including a solvent exchange procedure that elutes said organic solvent from the extrusion and replaces the organic solvent in the extrusion with said liquid; and
    removing said liquid form the extrusion so as to provide pores at locations at which said organic solvent has been interspersed with the polymer material during said extruding step, the method forming an elongated flexible and elastomeric suture material having an initially extruded length and a plurality of said pores and being axially stretchable up to about twice its said initially extruded length or more.

2. The method according to claim 1, wherein said polymer material is a urethane material which has elastomeric properties when extruded.

3. The method according to claim 1, wherein said liquid is an aqueous liquid.

4. The method according to claim 1, wherein said liquid is an aqueous liquid selected from the group consisting of water and a blend of water and an alcohol.

5. The method according to claim 1, wherein said organic solvent for the polymer material is selected from the group consisting or dimethylacetamide, dimethylformamide, dimethyl sulfoxide, tetrahydrofuran and pyrrole.

6. The method according to claim 1, wherein said extruding and passing steps form a single strand having an external diameter equal to that of a surgical suture, and said removing step and solvent exchange procedure provide a porous surface that promotes tissue ingrowth into said porous elongated flexible member.

7. The method according to claim 1, wherein said removing step forms a plurality of pores which have a pore size of on the order of about 0.005 and about 0.06 mm.

8. The method according to claim 1, further including attaching a needle member to a radially compressed end portion of said suture material.

9. The method according to claim 8, wherein said attaching step includes selecting said needle member to have an outside diameter that is smaller than that of said suture material.

10. The method according to claim 1, wherein said extruding step forms an elongated strand having an external diameter no greater than about 0.6 mm.

11. A method for manufacturing a non-braided porous and elastomeric polyurethane surgical suture, comprising:
    combining an elastomeric urethane material with an organic solvent for the urethane material in order to form an extrudable urethane mixture;
    extruding said extrudable material into an elongated polyurethane strand including a polymeric extrusion of said urethane material having said organic solvent interspersed with the polyurethane material;
    passing said extruded elongated strand of urethane material interspersed with said organic solvent into and through a supply of liquid within which said organic solvent is soluble and within which said polyurethane material is substantially insoluble, said passing step including a solvent exchange procedure that elutes said organic solvent from the extrusion and replaces the organic solvent in the extrusion with said liquid; and
    removing said liquid from the extrusion so as to provide pores at locations at which said organic solvent had been interspersed with the polyurethane material during said extruding step, the method forming an elongated flexible and elastomeric polyurethane suture material having a plurality of said pores.

12. The method according to claim 11, wherein said liquid is an aqueous liquid.

13. The method according to claim 11, wherein said liquid is an aqueous liquid selected from the group consisting of water and a blend of water and an alcohol.

14. The method according to claim 11, wherein said organic solvent is selected from the group consisting of dimethylacetamide, dimethylformamide, dimethyl sulfoxide, tetrahydrofuran and pyrrole.

* * * * *